United States Patent [19]
Benn et al.

[11] Patent Number: 6,104,827
[45] Date of Patent: *Aug. 15, 2000

[54] IMAGE ANALYSIS FOR MEAT

[75] Inventors: Alan Benn; David Barrett-Lennard; Peter J Hay, all of West Perth, Australia

[73] Assignee: Meat & Livestock Australia Limited, North Sydney, Australia

[ * ] Notice: This patent is subject to a terminal disclaimer.

[21] Appl. No.: 09/119,476

[22] Filed: Jul. 20, 1998

Related U.S. Application Data

[62] Division of application No. 08/318,839, Oct. 13, 1994, Pat. No. 5,793,879.

[30] Foreign Application Priority Data

Apr. 13, 1992 [AU] Australia ................................. PL1848

[51] Int. Cl.$^7$ ................................................. G06K 9/00
[52] U.S. Cl. ............................................ 382/110; 382/162
[58] Field of Search ................................ 382/110, 164, 382/165, 203, 204, 282, 257, 256, 241, 195, 190, 162, 199, 173; 348/89; 356/445

[56] References Cited

U.S. PATENT DOCUMENTS

| | | | |
|---|---|---|---|
| 4,226,540 | 10/1980 | Barten et al. | 356/445 |
| 4,413,279 | 11/1983 | Gorl | 358/107 |
| 4,665,554 | 5/1987 | Sternberg | 382/27 |
| 5,136,906 | 8/1992 | Antonissen et al. | 83/42 |
| 5,170,440 | 12/1992 | Cox | 382/22 |
| 5,172,423 | 12/1992 | France | 382/22 |
| 5,194,036 | 3/1993 | Chevaller et al. | 452/198 |
| 5,339,815 | 8/1994 | Liu et al. | 128/660.01 |
| 5,457,754 | 10/1995 | Han et al. | 382/128 |
| 5,793,879 | 8/1998 | Benn et al. | 382/110 |

FOREIGN PATENT DOCUMENTS

| | | |
|---|---|---|
| 0 369 596 | 10/1989 | European Pat. Off. . |
| 0 424 912 A2 | 10/1990 | European Pat. Off. . |
| 30 05 087 A1 | 8/1981 | Germany . |
| 259 346 A1 | 8/1988 | Germany . |
| 2 187 281 | 2/1987 | United Kingdom . |
| 2 258 916 | 8/1992 | United Kingdom . |
| WO 91/14180 | 9/1991 | WIPO . |
| WO 98/08088 | 2/1998 | WIPO . |

OTHER PUBLICATIONS

Choo et al., "Computation of Features of 2–D Polycurve–Enclosed Boundaries." Systems, Man, And Cybernetics, 1989 International Conference, pp. 1041–1047.

Chen, Y.R., McDonald, T.P. and Crouse, J.C., "Determining Percent Intra–Muscular Fat on Ribeye Surface by Image Processing." ASAE Paper No. 89–3009. The American Society of Agricultural Engineers, St. Joseph, MI, Jun., 1989.

McDonald, Tim, et al., "Location and isolation of beef carcass ribeyes in cluttered scenes." (Paper No. 89–3005 presented at ASAE/CSAE meeting, Jun. 25–28, 1989, Quebec, Canada).

*Primary Examiner*—Bhavesh Mehta
*Attorney, Agent, or Firm*—Bryan Cave LLP

[57] ABSTRACT

A process and apparatus for identifying a target section within an image of a meat section. Color data for each pixel is stored and the pixels having a predetermined color characteristic of the target section e.g. a certain red/green ratio, are discriminated. The process involves excising from a refined data set for the discriminated pixels at least one data set for a cluster of pixels representing an external image section which is adjacent to and contacting the target section but which does not form part of the target section, the excising step including analysing the shape of the refined image section represented by the refined data set to identify concavities and examining properties of links and/or properties of sub-sections formed by links to identify valid links demarcating the target section from adjacent touching external image sections. The refined data set after the excising step has been carried out is processed as the data set representing the target section of the image.

21 Claims, 6 Drawing Sheets

IMAGE ANALYSIS FOR MEAT

This is a divisional of U.S. Application Ser. No. 08/318,839, filed Oct. 13, 1994, now U.S. Pat. No. 5,793,879, which was the national stage of International Application No. PCT/AU93/00164, filed on Apr. 13, 1993, which claims benefit from Australian Application No. PL1848, filed on Apr. 13, 1992.

FIELD OF INVENTION

The present invention relates image analysis to locate a target section in an image. The invention has been developed for use in evaluation of meat quality parameters, particularly utilising contact-free determination, but the invention has wider application than this field alone.

BACKGROUND

In the meat industry it is becoming increasingly important for meat products to be accurately described to ensure that the correct products are directed to specific markets, maximum returns are gained for the different products and products can be changed over time to suit the requirements of the market. This is particularly so in the meat processing section of the industry which operates between the producers (farmers) and wholesale or retail consumers who purchase either whole carcases or boned-out cuts of meat in cartons. The requirements of the consumers (in various markets such as Australia, Japan, USA, Korea, EEC etc) are varied, with the potential for both large premiums and also heavy discounts for providing either the correct or wrong products respectively.

In the USA and Japan, for example, centrally controlled grading schemes have evolved to cater for this requirement by inspecting the carcases in the abattoir and assigning an overall grade to the meat products in the carcase which is based on several individual characteristics. The grading is based on an expert assessment of a cross section cut through the carcase at a specified site, usually between two particular ribs. This cut exposes several muscles, in particular the longissimus dorsi or ribeye muscle which is one of the more valuable portions of meat in the carcase, as well as intermuscular fat deposits, a cross section of the subcutaneous fat layer and any bones/ribs that may be present. Both US and Japanese grading schemes attach great significance in the grading schemes to the level of intramuscular fat contained within the ribeye (marbling), the colour of the ribeye muscle, the area of the ribeye and the colour of the intermuscular fat surrounding the muscles. These are all important quality measures although the ribeye area, intermuscular fat and subcutaneous fat thickness can also be used as a quantitative measure of the carcase by predicting the relative amount of meat in the whole carcase (i.e., lean meat yield %). In the US system the carcase is assigned a marbling category (slight, abundant, etc) based on comparison to a set of photographs published by the US Department of Agriculture (USDA), who are also responsible for training all graders within the industry. Meat colour is judged by reference to a few descriptive terms (bright cherry red, etc) and similarly for fat. Ribeye area is estimated in square inches but is mainly used to assign a yield grade rather than quality grade. Along with other characteristics (age, etc) these descriptions are used to assign the carcase/meat into a few overall grades ie premium, choice, select, etc.

The Japanese grading system, for example, goes a stage further by having a reference set of artificially made 'chips' which are used for comparative scoring of meat colour, fat colour and marbling. Thus, an individual carcase can be given a score of marbling (1–12, indicating no fat to abundant fat) meat colour (1–9, indicating light to dark) and fat colour (0–9, indicating white to dark/yellow) where the marbling score in particular has a great bearing on the value assigned to the meat.

In Australia, AUSMEAT have developed a Chiller Assessment Method which is similar to US and Japanese methods. Usually, the assessor is also trained to make objective measurements of subcutaneous fat depth at a particular site with a ruler, and ribeye area using either a grid and manual counting technique or a digitising tablet which computes the area from an outline traced around the ribeye boundary with a stylus.

A typical abattoir processing >500 carcases per day would need to train several skilled, senior personnel to be qualified chiller assessors to cope with assessing every carcase. These assessors would typically be required to start early (ie be paid penalty rates), would require expensive, ongoing training and be subject to variability between their assessments.

Papers have been published by Chen and McDonald (Chen and McDonald, Proc. 1989 ASAEICSAE meeting. & Chen and McDonald, Trans ASAE, 33 [6], November 1990.) These papers describe techniques for the identification of the ribeye muscle from among the image of the total cross section and also for the measurement of the marbling score on a given ribeye muscle. The papers do not describe a hardware system in any detail but concentrate on the software/signal processing methods for performing the image analysis. It appears that all development work was based on photographs taken of quartered carcases for the ribeye descrimination work and 6 USDA marbling standard photographs for the marbling work. The whole technique as disclosed is based on the use of monochrome images.

A prior art technique for delineating the ribeye muscle is based on 'morphological operations' to separate muscles which are directly adjacent to the ribeye muscle.

A prior art discrimination technique essentially revolves around a 'fixed gray level thresholding' method, with some pre-processing to remove large scale variations due to lighting variation across the sample/image.

Earlier patents have also tried to make use of automated methods for evaluating the quantitative and qualitative characteristics of the rib section. Examples are provided in U.S. Pat. Nos. 3,154,625 (Oct. 1964), 4,226,540 (Oct. 1980), 4,413,279 (Nov. 1983).

U.S. Pat. No. 4,226,540 discloses the use of a video cambera but uses only very basic methods for attempting to quantify the relative amounts of fat and meat in the sample.

Another field of use of an image analysis system is in assessment of retail cuts of meat. For example, a purchaser of large quantities of meat cuts, e.g. a catering establishment supplying a hospital or airline, needs to monitor the quality of meat cuts being supplied and such monitoring needs to be as consistent and objective as possible. Similar parameters to carcase assessment parameters need to be measured, although other meat sections may be involved, e.g. tenderloin, striploin, tenderloin centre cut, etc.

Assessment of other objects may also usefully employ an automated image analysis system, e.g. assessment of fish, fruit, manufactured food products, or other natural or manufactured articles.

OBJECTS OF INVENTION

It is an object of the present invention to provide aprocess and apparatus for identifying a target section within an image to enable processing of data concerning the target section.

It is a further and preferred object of the present invention to provide a process and apparatus particularly suitable for automatically analysing meat quality parameters.

A further preferred object of the present invention is to provide a process and apparatus adapted to provide repeatable and reliable evaluation of meat quality.

SUMMARY OF THE INVENTION

According to the present invention there is provided a process and apparatus for image analysis as defined in the appended claims.

The colour data are conveniently the red, green and blue components of the image at each pixel since such data are readily derived from signals from conventional colour television cameras and image analysers, but other or additional colours including "colours" beyond the visible spectrum, may be useable. In the case of meat analysis, the predetermined colour characteristic may be the red component at each pixel. The selected pixels which the refined data set represents need not be only those pixels having the predetermined colour characteristic but may include those which are wholly enclosed within the boundaries of the shape defined by the refined data set (e.g. pixels representing intramuscular fat in the ribeye muscle).

The present invention when used for meat quality assessment in an abattoir or other meat processing facility utilises a system based on the technology of image analysis which can accurately, automatically and objectively measure all five of the parameters assessed within the Chiller Assessment System (CAS) and can have inbuilt capabilities for the determination of a number of other quartered section parameters (eg: percentage of fat in section, shapes, marbling characteristics, intermuscular fat characteristics, etc). The current prior art manual technique is relatively slow (1–2 mins/carcase), labour intensive and subject to potential errors or abuse through its independence on human, subjective assessment by personnel employed by the abattoir. The image analysis system provides a high speed (10 s/carcase), automated assessment technique which requires unskilled labour for operation (to position the camera over the meat section) and which can guarantee impartiality, accuracy and consistency of standards. The basic techniques of the present invention is measuring the various aspects of the cut section can be applied to any grading standard.

The CAS based on Video Image Analysis (VIA) alleviates the overall problem associated with manually based techniques regarding their overall practicality for industry. The VIA based system can keep pace with the on-line throughput of the fastest abattoirs (250–400/hr), and can be relied on to provide a consistent, accurate assessment. The overall operating costs have also been shown to be cheaper than an equivalent manual system by a thorough cost:benefit analysis.

Representation of a meat portion, preferably by means of spatial Red, Green and Blue pixel information serves to enable determination of various meat quality parameters. This applies equally to retail meat custs evaluation and other product evaluation based on colour characteristics.

BRIEF DESCRIPTION OF THE DRAWINGS

A preferred embodiment of the present invention will now be described with reference to the accompanying drawings, wherein.

DETAILED DESCRIPTION OF THE INVENTION

The present invention makes use of a solid state, full colour RGB camera coupled to a high resolution image digitiser board which allows sophisticated, high speed image processing to extract highly detailed information from the images, corresponding closely with the same information obtained by an expert human assessor.

The present invention utilises colour differences between meat and fat to provide a discrimination and identification of fat particles within a meat carcase. Preferably, these colour differences refer to hue, saturation and intensity variations and ratios of red, green and blue etc, however other parameters may be optionally incorporated. The present invention also utilises an adaptive, localised thresholding technique (as herein described) to cope with variations in local meat colour, whether due to lighting variations or actual meat colour variability.

OVERALL SYSTEM

Figure 1:
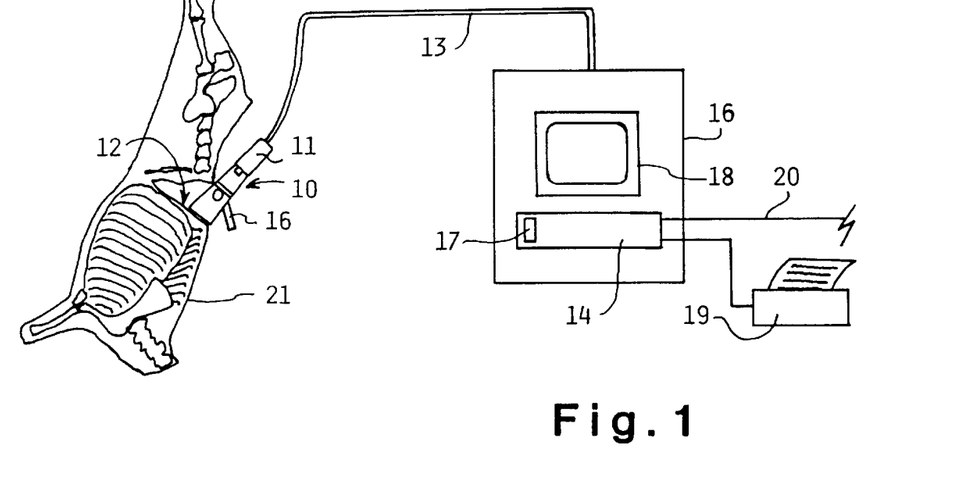
FIGS. 1, 2, 3 and 4 show an apparatus in accordance with the present invention.

FIG. 1, shows the main system components of the VIA meat quality assessment system. These components are a camera frame assembly 10 which is used for rapid, repeatable alignment of the camera 11 with respect to the exposed meat section 12. (2) Cables 13 transfer video signals to the computer 14, control information between the operator and computer and power to the camera 11, lamp 15 and keyboard 16. Waterproof cabinet 16 houses the computer 14 containing appropriate image analysis software and an image digitising and image analysis board 17. A colour monitor 18 displays images from the video camera 11 and operates during the processing of the image and provides information/results to the operator. A printer 19 for obtaining hard copy results or for printing special labels for direct attachment of results to the carcase being assessed. Communications link 20 goes to a central abattoir control computer. The half carcase 21 being assessed, which has been 'ribbed', which involves making a knife and saw cut partially through the carcase to expose the cross section 12 through the carcase back. A small amount of tissue is left between the lower part of the carcase (forequarter) and upper half (hindquarter) to maintain the carcase as a single unit. The ribbing site varies but is typically between the 12/13th, 10/11th or 5/6th ribs. The camera frame 10 is typically used as shown in FIG. 1, but could also be used on fully quartered carcases or sections cut and fully or partially removed from either the fore or hindquarter, ie primal cuts.

Figure 6:
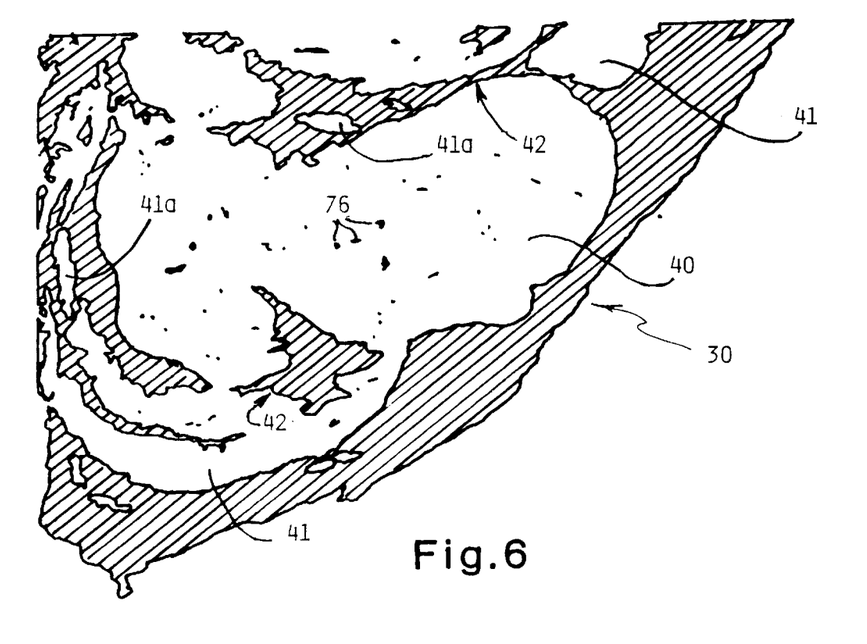
FIG. 6 shows a binary representation of a typical rib-section image.

The camera frame 10 provides a repeatably positioned image of the rib section to the image digitiser in the computer 14 after being manually positioned. A typical image 30 is shown in FIG. 6 although in the computer this is in the form of a full colour image.

The process of image digitisation involves translating the analog electronic signals from the camera 11 into arrays of (typically) 512×512×8 bit digital numbers for each of the 3 colour signals—red, green and blue. Each number in the array is referred to as a 'pixel' of the image and the 8 bit value of the pixel indicates the intensity of colour information at that pixel location in the image. The position of the number in the 512×512 array references the spatial location of the pixel in the image in an x - y co-ordinate sense. Corresponding x - y positions in each of the 3, 512×512 arrays reference the red, green and blue (RGB) intensities respectively, of a single pixel and so indicate the colour of the pixel to within a resolution of 3×8 or 24 bits ie approximately 16 million colours. The arrays of numbers are typically held in electronic memory components on the image digitising board 17 referred to as the frame buffer.

The image analysis procedure refers to software and algorithms contained within the outer 14 to process these arrays of numbers to extract information regarding the particular object being imaged. This may involve for example, determining the extent of the object within the frame buffers which by suitable calibrations can be used to calculate the size/area of the object. Also the colour can be determined by analysing the pixel values corresponding to the object position in the frame buffer.

The colour monitor 18 is used to show a live video image from the camera 11 while the frame 10 is being positioned. At the operators indication via a keyboard terminal 10 on the frame, the image 30 is digitised and the fully automated analysis procedure commenced. Results of the analysis and other important information regarding system operations are also shown on the monitor. These results can be downloaded as required to local ticket printers or remote computer systems.

SYSTEM COMPONENTS

Figure 2:
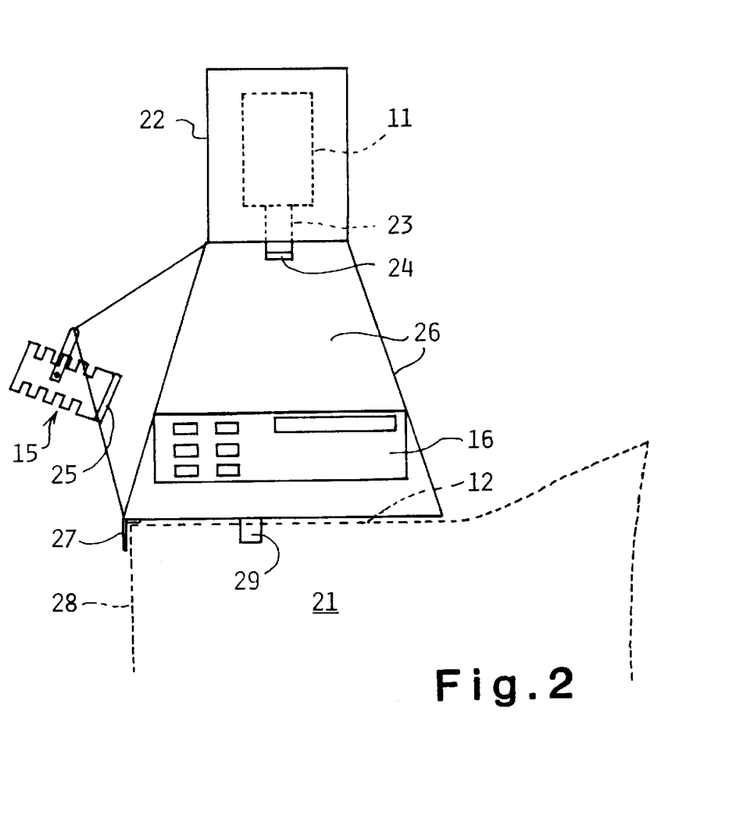
Figure 3:
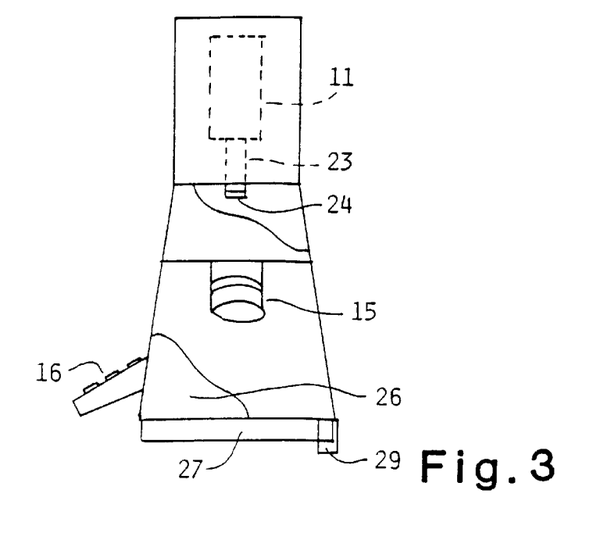
Figure 4:
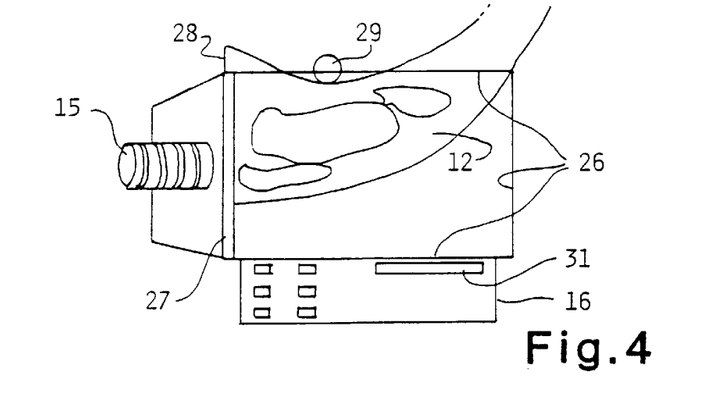

More detailed diagrams of the camera frame assembly 10 are shown in FIGS. 2,3 and 4. The frame has been specifically designed for rapid, easy operation on quartered carcases but can also be used on primal cuts or other meat samples.

The frame essentially comprises: a solid state RGB video camera 11 mounted within a stainless steel 'cover' 22 and with provision for accurate alignment of the camera to the frame viewing area. The camera lens 23 is designed to view the area enclosed by the bottom rectangle of the frame assembly and encompassing typical sizes of rib sections from a wide variety of carcase types and sizes. The lens 23 is fitted with a polarising filter 24 which is arranged to be orthogonal to a similar polarising filter 25 mounted on the lamp assembly 15. The lamp assembly has been designed to provide uniform, diffuse illumination across the whole viewing area which is achieved through the internal lamp construction, the arrangement of the lamp at a shallow, inclined angle to the viewing surface and the provision of matt reflectors 26 surrounding the other three sides of the frame 10 apart from that occupied by the lamp assembly 15.

Positioning of the frame on the cut rib section is guided by a section of right angle steel 27 at the bottom of the frame which is used to locate against the 'sawn chine' 28 of the carcase. The sawn chine is the surface where the hanging carcase has been cut in half vertically through the vertebrae and so is a relatively firm, accurate edge against which to reference the cut section. Secondary orientation is facilitated by a lug 29 which protrudes from the bottom of the frame. This lug 29 is located against the inner rib surface of the carcase and effectively positions the rib section image at the top of the image viewing area and again provides a reliable, anatomical reference (see FIG. 4). Finally, the general frame assembly is positioned parallel to the sectioned surface 12 by pressing the frame down onto the meat surface. The chine locating device 27 has a horizontal protrusion which accurately aligns the frame coincident with the meat surface at the sawn chine.

A keyboard terminal 16 is also provided to enable the operator to control the system operation, ie initiate analysis, enter other carcase details such as identification number, body weight etc. This terminal also carries a single line display panel 31 to relay system messages to the operator who then does not need to reference the main monitor 18.

Figure 5:
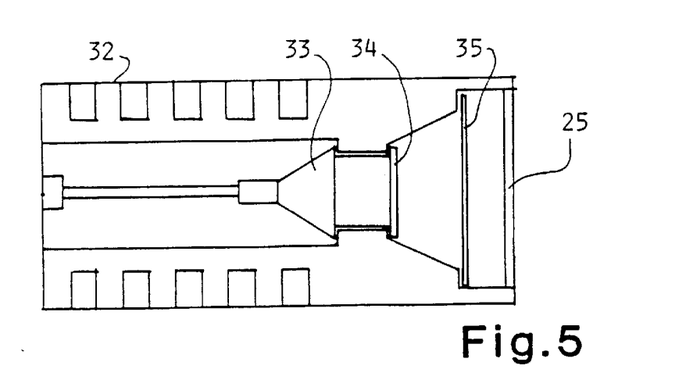
FIG. 5 shows a lamp assembly for use with the apparatus of FIGS. 1, 2, 3 or 4.

The lamp assembly 15 is shown in detail in FIG. 5. The assembly comprises a finned, heatsink housing 32 containing a 12 v dichroic lamp 33 providing a stable, efficient light source with a colour temperature of 3200° C. The infra red filter 34 is provided to block infra-red radiation from reaching the diffuser 35, polariser 25 and the meat surface and so restrict heat damage to all three of these items. The diffuser 35 ensures that the light output from the lamp 33 is spread more uniformly over the viewing surface than would result from the typical beam distribution of the lamp. The polarising filter 25 allows only light of a specified polarisation direction to illuminate the meat surface. With the polarisation direction arranged vertically, this reduces specular reflection from moisture on the meat surface and so prevents artefacts due to these reflections appearing in the images. This is also assisted by the polariser 24 on the camera lens 23 which is arranged in such a position as to minimise specular reflections while allowing diffuse reflections from the general meat and fat surfaces to create the image 30 in the camera.

IMAGE ANALYSIS SOFTWARE

The system is currently designed to automatically measure the five main components of the Ausmeat CAS:
(a) ribeye area (cm2),
(b) marbling score (% of ribeye area covered by fat),
(c) meat colour (RGB or HSI relative to white standards),
(d) fat colour (RGB or HSI relative to white standards),
(e) subcutaneous fat depth (mm, at a specified location).

These variables can be made completely general and applied to, for example, USDA and Japanese grading methods with a suitable calibration to convert the absolute measurements above into the required grading standards. This has been done for the AUSMEAT system by calibrating measured marbling fat percentages to marbling scores assigned by expert assessors and similarly for meat colour values to meat scores and fat colour values to fat scores. The inherent colour measured using the digitised pixel values (RGB intensity as 3 8-bit numbers) can be converted by an algorithm to an alternative colour measurement system referred to as the HSI (Rue, Saturation and Intensity) colour space. These 'indirect' measurements are easier to work with and provide more understandable calibrations to subjective scores than the raw RGB values.

The techniques also make available a wide range of other parameters (over and above those used for Ausmeat CAS analysis) which can be easily measured and which can be related to other quantitative and qualitative characteristics of the carcase eg: carcase yield percentage, meat tenderness etc. Examples of other measures are:
  percentage of fat in the whole section;
  percentage of meat in the whole section;
  intermuscular fat thickness/area;
  other muscle areas;
  marbling shape and distribution characteristics;
  muscle shape characteristics.

The sequence of the five Ausmeat analysis components is only critical in that the ribeye area should conveniently be accurately identified before marbling analysis, meat colour and fat colour are measured. (The AUSMEAT fat colour measurement site is referenced to the ribeye position). Measurement of subcutaneous fat depth is essentially independent of all other processes and the above order will be followed in further descriptions of the software.

LOCATION OF RIBEYE MUSCLE IN THE RIB SECTION

FIG. 6 shows the problems faced in identifying the ribeye muscle 40 in the rib section image 12, the main problem being that when there is no clearly identifiable boundary between directly adjacent muscles 41, (usually a layer of intermuscular or 'seam' fat 42), then very sophisticated techniques need to be applied to find the correct separation point.

It is assumed that we are given a 512×512×24 bit colour image of the rib cross section of a left hand side beef carcase. It is imaged in a standard fashion—with the sawn chine along the left hand edge, and the trough of the ribs at the top edge. Use of the camera frame 10 also guarantees a known pixel-to-mm conversion factor in both the x and y directions. 'x' directions refer to a left to right direction in the accompanying diagrams while 'y' directions refer to a top to bottom direction. Similarly x and y distances refer to differences in pixel locations in the appropriate direction.

STEPS

The processing is typically described as a sequence of 19 steps which are applied one after the other.

Figure 7A:
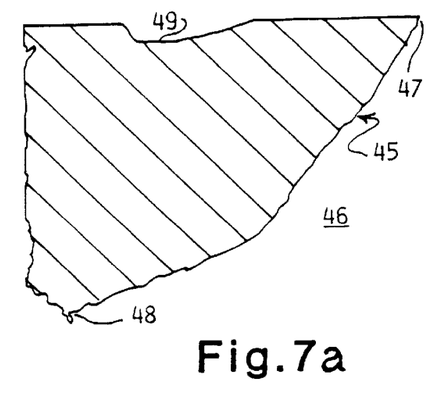
FIGS. 7 to 17 show portions of a method of assessing meat quality in accordance with the present invention.
Figure 7B:
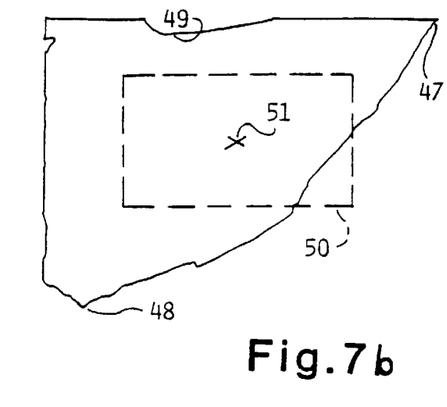
Figure 9:
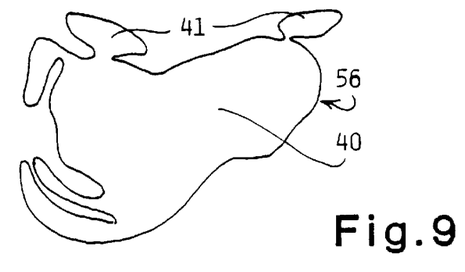
Figure 10:
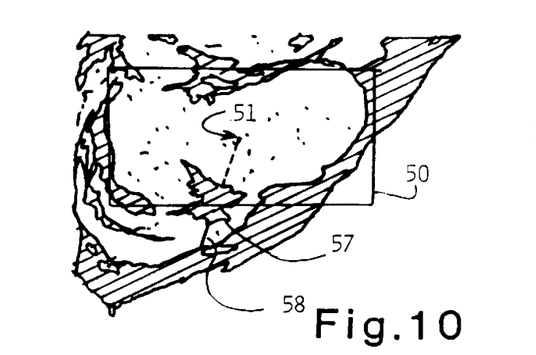
Figure 11A:
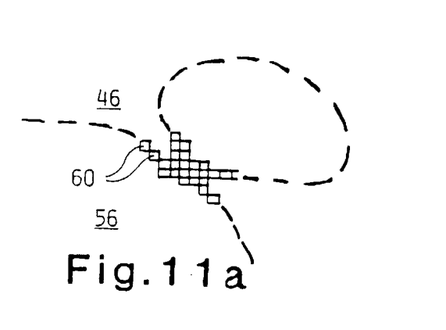
Figure 11B:
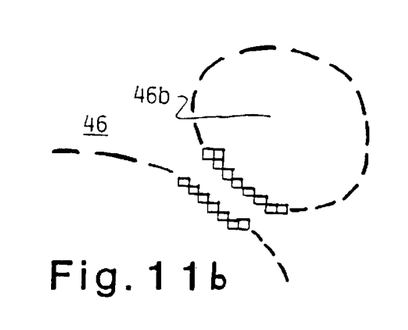

1. Threshold to find the area of interest (AOI):
   To identify the general cross section against the background, a fixed threshold is applied to the entire image 30 in the Red frame buffer to generate a binary image 45 (FIG. 7a) ie all pixels with Red>threshold are regarded as the rib section (AOI) and all others are classified as background 46.
2. Search for the largest object: A scan is done downward from the midpoint of the top of the screen until an object with at least, 500 'edge' pixels is located. The edge of the object is traced and stored in memory as an array of (x, y) co-ords.
3. Search for (endx, endy), (bottomx, bottomy) and (ribx, riby):
   Using the edge of the area of interest a search is made for the right most point (endx, endy) 47, the bottom/left most point 48 on the subcutaneous fat layer (bottomx, bottomy) and the lowest point (ribx, riby) 49 in the trough of the ribs.
4. Calculate the 'ribeye box':
   The 'ribeye box' or calculated target zone 50 is a rectangular estimation of the ribeye and is determined by prediction from the (bottomx, bottomy), (endx, endy) and (ribx, riby) points 47, 48, 49. This method of prediction has been found by experience with a large number of section images to provide a sufficiently reliable, indicative location of the ribeye 40.
5. Calculate the seed point:
   The seed point 51 is preferably the centre of the ribeye box 50. It is not essential that the seed point 51 is the centre of the ribeye box. It is essential that the seed point is a point that corresponds to ribeye meat. The point may therefore be at any relevant location in the ribeye box, however a centre point has been found to most reliably correspond to ribeye meat. It is used in later processing to measure directions of vectors and for seeding a flood fill operation.
6. Threshold the image: The colour image is thresholded by independently evaluating the R,G,B values of every pixel. The intention here is to bias the threshold towards fat—i.e. to bring out any wisps of fat which facilitate the easy removal of external muscles attached to the ribeye.
   A globally fixed threshold is applied. The main meat/fat discrimination can be explained as a line 52 on a plot of the red versus green values of the pixels in a typical rib section image (see FIG. 8). Essentially all pixels with a R/G ratio above a prescribed value are regarded as meat (area 53 and pixels less than this ratio are fat (area 54). More sophisticated techniques have also been developed for performing the initial meat-fat discrimination eg: using the same method as described below for marbling analysis, statistical discrimination techniques etc and may be applied if desired.
   Pixels with R less than a fixed threshold are assumed to be background (area 55).
7. Paint J:
   From the defined seed point 51 the meat is painted as the general target area 56 comprising a single CONNECTED piece referred to as J.
   Typically J covers the ribeye muscle 40 plus possibly some external muscles 41 which are directly adjacent to the ribeye and not separated from it by a 'seam' of fat 42. Any meat (see 41a in FIG. 6) not so connected to the ribeye 40 will not be painted and hence is discarded (see FIG. 9).
8. Fat Blob Scan and application of 'cuts':
   J is scanned for its internal fat blobs which have been identified by the initial fat meat threshold. As they are found they are traced, polygonised and stored away.
   However, some fat blobs are particularly large e.g. blob 57, and are judged to be intermuscular fat. In this case they are not stored away but rather a 'cut' is performed as shown in FIG. 10.
   The criteria for applying a cut 58 is dependant on the number of edge pixels in the fat blob 57, the distance of the centroid of the fat blob into the model box 50 and the area of the fat polygon.
   To apply a cut (see FIG. 10)
   (a) consider the ray from the centre 51 of the ribeye box 50, out to the centroid of perimeter of the fat blob 57,
   (b) search for the edge pixel of the fat blob which is close to where the ray passes out of the fat blob 57,
   (c) a double thick line (4) is drawn from this edge pixel out to the border of the screen along the direction defined by the ray and in a colour to simulate a seam of fat, thus artificially connecting this fat polygon 57 to the rest of the intermuscular fat 42.
9. Apply an opening to J:
   'Erode' J by repeatedly tracing around its edge and drawing the same pixels 60 in the colour of the background 46 (FIG. 11a). Any areas of meat 41b disconnected from the ribeye by this process are removed (FIG. 11b). Do the same number of 'dilations' to J to bring it back to its previous size.
   This removes some of the muscles 41b which were only attached to the ribeye 40 by a narrow bridge of meat (ie had a small gap in the intermuscular fat layer) and tends to smooth the outline of J. The smoothing effect is useful to reduce the complexity of J and enable faster processing.
10. Trace and polygonise J:
    J is traced to identify the edge which is then 'polygonised'. This is achieved by beginning with a very coarse polygonal approximation to J and recursively splitting the segments which are not sufficiently close to the true edge into two separate segments. This technique is well described in the literature.

Figure 12:
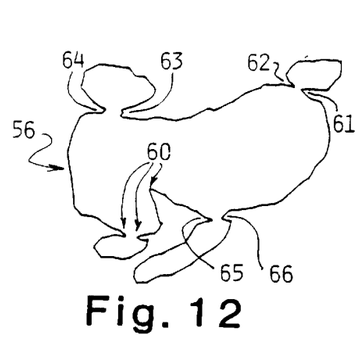
Figure 13:
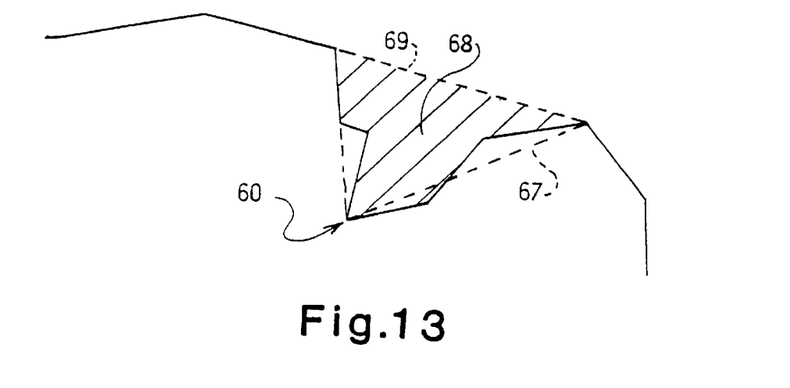

11. Find the concavities of J:

The 'concavities' 60 of J provide very useful information regarding the likely locations of external muscles 41 which need to be chopped away as shown by points 61 to 66 in FIG. 12. The concavities 60 to 66 are quantified as to their 'goodness' by considering the area 67 enclosed by the triangular region defined by the sides of the concavity, the actual area 68 enclosed by J within the same region and the length 69 of the baseline of the triangular region FIG. 13).

12. Process J:

Some initial processing of J is done to remove obvious external muscles.

Figure 14:
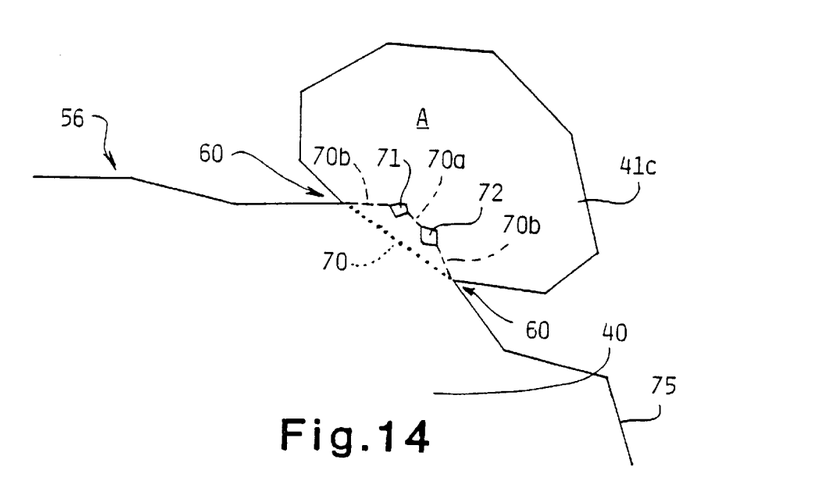

Steps:

1. Loop through all pairs of concavities 60 to 66 of J.
2. Check that each link is valid (i.e. it must not pass outside J).
3. Measure the following parameters for the link (FIG. 14):
    (a) the length L of the link 70,
    (b) the area A to be discarded. This is assumed to be the smaller 41c of the two areas that J is broken into by the link,
    (c) the strength W of the wisp under the link 70; this is calculated by considering the values of GREEN (the best discriminator between meat and fat) in the image in the vicinity of the link. The average GREEN is measured along all the pixels in the link 70 and similarly in line segments parallel to the link but offset to either side. From this information we can get a profile of GREEN as we pass from one side of the wisp to the other. The strength W of the peak is measured,
    (d) the criteria for applying the link 70 is based on L, A/L*L and W. Note that A/L*L is a dimensionless quantity which is a measure of the aspect ratio of the piece being discarded. Thus sections 41c of J with a high aspect ratio, short length of joining to the ribeye and with a wisp of fat present along the joining line 70 will be removed.

13. Match J to the database:

A database of actual ribeye shapes have already been found and stored in memory as a list of polygons. J is matched to each of these polygons in turn to find the polygon in the database which most closely matches J. J typically contains the ribeye 40 plus extra muscles 41, so a matching scheme which does not unduly weight those parts of J where the match is particularly bad is used. In effect the percentage of the model which aligns well with some part of J is calculated.

14. Find links from fat:

Typically an external muscle 41 attached to the ribeye 40 results in two concavities 60 on J (area 56) between which there is a string of fat blobs 71, 72. The aim of the next section of software is to find these 'paths of best separation' between the concavities ( see FIG. 14). The first stage is to find neighbouring fat blobs 71, 72 and store away all the links 70a between them.

(a) Given a fat polygon 71, find all the other fat polygons 72 in the vicinity. A link 70a between two fat polygons 71, 72 is defined as the directed line segment between the two closest vertices.

(b) Discard links that are directed 'anticlockwise' around the ribeye, (c) Discard redundant links ie the longer of two links from the same vertex which essentially travel in the same direction, (d) Discard links that pass outside of J, (e) Discard links that don't match well to the model being used from the database.

15. Find links 70b from concavities 60 of J:

This follows the same methods used for finding the links from the fat polygons but considers links to fat polygons 71, 72 and directly to other concavities 60 of J. All the same discard tests are applied. These links 70b are used to start off the chain growing.

16. Chain growing:

Depth first tree searching is used to find all the possible chains 70b, 70a, 70b of links which cut up J. This algorithm is exhaustive in that it will find ALL chains (the only restriction is that the chains must have a prescribed maximum number or less intermediate fat polygons 71, 72).

The following is done for each of the concavities (ie startvertices—'startv') of J to produce finished chains:

(a) Find all the outgoing links from startv. Links to another concavity of J represent finished chains.

Links to fat polygons are all pushed onto a stack.

(b) Repeat while the stack is not empty.

Pop a link off the stack. This gives us the current fat polygon we are on.

Links to concavities of J represent finished chains.

Otherwise links to fat polygons are all pushed on the stack, unless we have exceeded the maximum allowed number (eg: 5) of intermediate fat polygons for a chain.

17. Choose Best Chains From Redundant Sets:

Large numbers of redundant chains are produced by depth first tree searching. In particular there are typically many chains which form between two given concavities of J. The best representative chain of a group that all start and finish on the same concavities is selected to be the chain with the minimum distance over meat areas.

18. Test validity of finished chains (70b, 70a, 70b).

The following parameters are calculated for all the chains:

| | |
|---|---|
| direct length: | the direct distance from the start vertex to the end vertex. |
| chainlength: | the total length of the chain. |
| meatlength: | the distance travelled over meat areas, ie the sum of the lengths of the links used to leap frog between a sequence of fat polygons. |
| remaining area, chopped area: | J is chopped by the chain into two pieces. |
| Qchain: | The chain is matched against the model using the same method by which J was matched to the database. This parameter represents a percentage of the length of the chain that coincides with the model. |
| Qreplace: | The section of the perimeter of J that is to be discarded by the chain is matched against the model. |
| wisp: | The wisp strength is found by taking a weighted sum of all the wisp strengths of the links forming the chain. |
| bandwidth: | The normal distances to vertices on the chain from the direct line segment are measured. The range gives the bandwidth of the chain. |
| straightness: | = 100 * directlength/(bandwidth + 1). This gives a measure of the straightness of the chain by evaluating the aspect ratio of the rectangle containing the chain. |
| turnbackdist | The chain is made up of a sequence of linear |

-continued

| | |
|---|---|
| | segments. Each of these is projected onto the direct path. The total distance travelled backwards is calculated in this way. |
| turnbackperc: | = 100 * turnbackdist/directlength. The percentage turn back in the chain. |
| chopped aspect: | = chopped area/meatlength$^2$. This is the A/Lsqd aspect ratio determination for the section of J to be chopped away. |
| chopped height: | = chopped area/direct length. This is a measure of the size of the section to be chopped away. |
| cut in area: | the area of the intersection of the model with the section to be chopped away. This is used as an estimate of how badly the chain has cut into the model (if at all). |
| vertex concavity qualities: | There are four to evaluate:- 1. start vertex before apply chain 2. end vertex before apply chain. 3. start vertex after apply chain. 4. end vertex after apply chain. |
| Meat area percent: | this measure calculates the total meat area in the section expressed as a percentage of the total section and makes use of known data to establish a further quality measure, for example if the total meat area percentage in the section is greater than one would normally expect, this lends weight to any decision being made concerning the removal of a muscle. |
| chain quality: | A linear combination of chopped aspect, Qchain, Qreplace, wisp and other measures as described above. This is the main chain quality measure which combines the local knowledge (A/Lsqd) with the database match. |

Several of the individual criteria measured for the chains can be used to eliminate the chain from consideration as a 'valid' chain. eg turn back percentage is too high.

19. Apply chains to J

The chains which are determined to be valid are not necessarily applied to J. A local best feature is still required to only select out a single chain from a number that are doing essentially the same thing. This is achieved by ordering all the valid chains according to their quality measure. They are then considered in order from best to worst and the first chain is applied to J. In the process, J has a section 41c removed. As a result, when other chains are applied their quality measures will be altered (in particular the area chopped away by another chain will often be less), hence later chains find it more difficult to be applied.

MARBLING ANALYSIS

Having located the boundary 75 of the ribeye muscle 40, marbling analysis involves quantifying the relative surface area that is occupied by fat 76 (FIG. 6) as opposed to meat. The analysis can also involve quantifying the sizes and locations/distribution of the individual fat particles 76 throughout the ribeye 40 and weighting these accordingly. The stages of marbling analysis are:

(a) discrimination; to examine each pixel in the ribeye area and determine whether it represents fat or meat in the image, thus creating a binary image comprising fat and meat; 17

(b) fat % calculation; by calculating the total number of fat and meat pixels (nfat and nmeat respectively) within the ribeye, the relative percentage of fat is readily calculated ie.

fat %,=100*nfat/(nfat+nmeat)

it is also convenient at this stage to calculate ribeye area.

ribeye area=(nfat+nmeat)*xscale*yscale Where xscale and yscale represent the x and y dimensions (in cm) of an individual pixel and which are readily determined by imaging objects of known size.

(d) Optionally convert the marbling fat % to a standard score by referencing a previous calibration eg fat %=0 to 2% is equivalent to score 1.

The discrimination technique typically used is based on a combination of colour discrimination similar to that applied for finding the meat/fat areas in the whole section, and a dynamically applied local thresholding method to locate small faint particles of fat, particularly in lighter and darker areas of meat.

Figure 8:
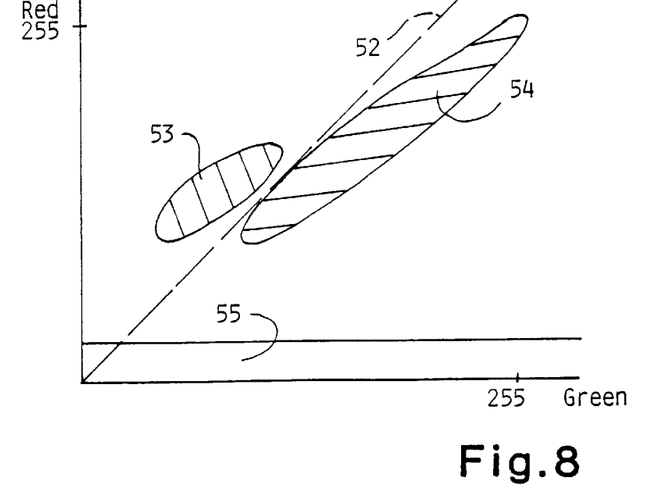

The first stage uses a linear colour discrimination method based on the Red and Green values of all pixels as previously described in FIG. 8. This generates a binary image corresponding to the ribeye and surrounding areas, where pixels categorised as 'definitely meat' are labelled. To be this confident the discrimination line is shifted relative to the previous situation such that only pixels with a strong R/G ratio are classified as meat, thus pink or light meat will not be so classified.

The whole area of analysis is then divided up into equally, sized boxes (eg 16×16 pixels in the x and y directions). Within each box the average green value of all pixels classified as definitely meat is calculated (Gmeat). The relative green values on meat and fat have been found to provide the best discrimination between the two categories (ie largest difference in values), however if a global (ie whole image) threshold value of green is used to separate meat from fat (ie fat=G>threshold), a very poor discrimination results, especially in areas where the meat colour varies. This is improved by using a local threshold within each 16×16 box of the image. The local threshold is calculated linearly from the Gmeat value previously calculated.

ie local G threshold=a+b*Gmeat (where a and b are empirically determined constants for the particular meat)

The threshold is then performed such that all pixels with G>Gthreshold are classified as fat. Thus, in areas where the meat is dark (G low), G threshold is also low and fat that may be less bright than fat in other areas will be correctly classified. This process is repeated in every box until a binary image covering the ribeye area is produced. The final stages of calculating fat % and score are then straightforward.

A refinement to the above technique is required when and if within any box, only a very small number of 'definitely meat' pixels are found, then the average green value (Gmeat) may not be reliable. In this case the Gmeat values from directly adjacent boxes are used to provide the threshold.

An additional or alternative method can be used to measure meat colour. As before the meat section is initially identified by means of a thresholding operation. Previously the meat colour was then found by averaging the pixel colours within that section. In the alternative method, however, a histogram is generated of pixel colours within the section and operations are made on that histogram to identify the meat colour. This method has the advantage that it is less confounded by the presence of marbling within the meat section. The histogram method achieves performance enhancements by ignoring those pixels that are artificially "lightened" by the fact that they partially overlay marbling fat that would otherwise unfairly bias the meat colour average.

MEAT COLOUR ANALYSIS

Meat colour calculation is actually combined with marbling analysis while the binary mask indicating whether each pixel is fat or meat is available. By using this mask and the ribeye boundary 75, the colour of all meat pixels within the ribeye 40 can be calculated. This provides an absolute method of colour measurement providing the system has been suitably calibrated (as described below). The absolute colour values can be converted into a standard score by a suitable calibration eg if 36<intensity<45 then score=4, or score=19−0.2*intensity.

FAT COLOUR ANALYSIS

This is very similar to the above description for meat colour with the main difference being that the site 80 at which the fat colour is to be measured must be defined. Within the Ausmeat system this is defined as a small region of intermuscular fat directly adjacent to the ribeye muscle 40 as shown in FIG. 15.

Figure 15:
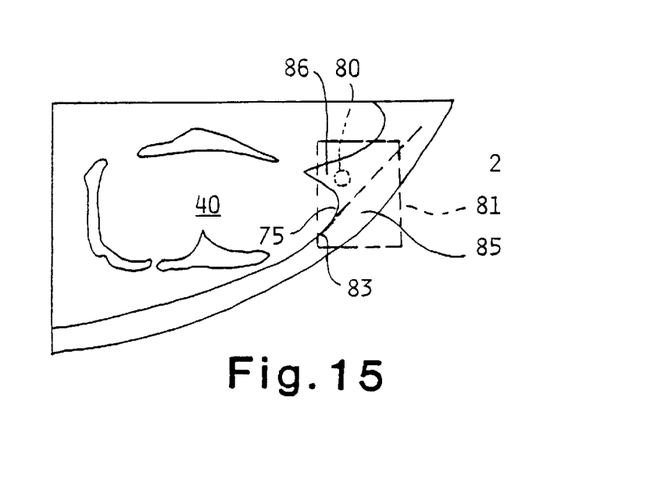

The method for locating this site is to first define a search area 81 with respect to the ribeye boundary 75 as shown in FIG. 15. Within this area the marbling fat-meat discrimination is performed to identify fat pixels but with a bias to detect only "bright, clean fat". A line 82 is them drawn parallel to the subcutaneous fat edge, starting at a point 83 previously located at the bottom-right extremity of the ribeye edge. This line 82 is used to separate essentially all subcutaneous fat 85 from the intermuscular fat 86. The average RGB value over the remaining fat area is then measured.

SUBCUTANEOUS FAT DEPTH MEASUREMENT

Points 47, 48 previously calculated in the analysis for finding the ribeye 40, ie bottomx, bottomy, endx, endy are used here to define a default 3rd order polynomial in x and y co-ordinates which models the expected position of the edge 87 of the subcutaneous fat 85. The line 88 (FIG. 16) described by this polynomial is divided into a number of discrete uniform intervals 89 to provide a sequence of points 90 along the line. At each of these points a 'search line' 91 is generated perpendicular to the polynomial 88 and of fixed length spaced equally on either side of the search point 90. The green values at each of the pixels under the search line 91 are read into a buffer to create a 'line profile' of green intensity across the fat layer, see FIG. 17.

The intensity profile is first searched to obtain the maximum value 92, Gmax. The profile is then segmented to provide a straight line approximation 93 to the profile and so ignore small, noisy deviations. The segmented profile is then searched for a segment where the start and end values of intensity on the segment differ by more than a fixed percentage of Gmax 92.
ie search for G(end)−G(start)>0.8*Gmax This is typically found and so marks the leading edge of the subcutaneous fat layer as being within this segment. The actual edge position is defined as between the two pixels whose difference in Green values is a maximum within the range of the segment ie the position 94 of maximum slope. If the threshold of 0.8*Gmax is not exceeded, the threshold is reduced gradually until either a segment is found, or the threshold reaches 40, at which stage the search is abandoned and the fat edge is not located on this search line.

Figure 16:
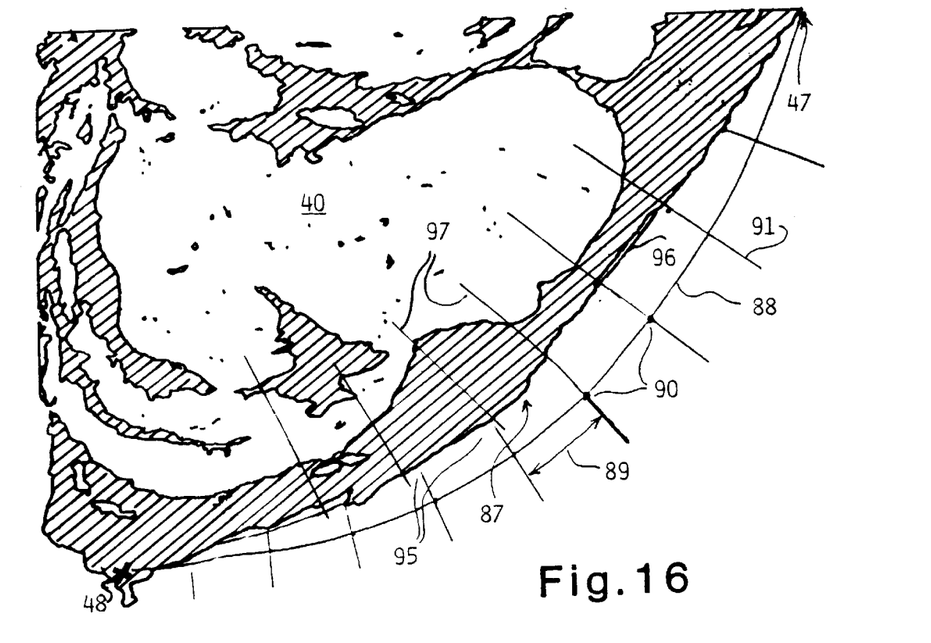
Figure 17:
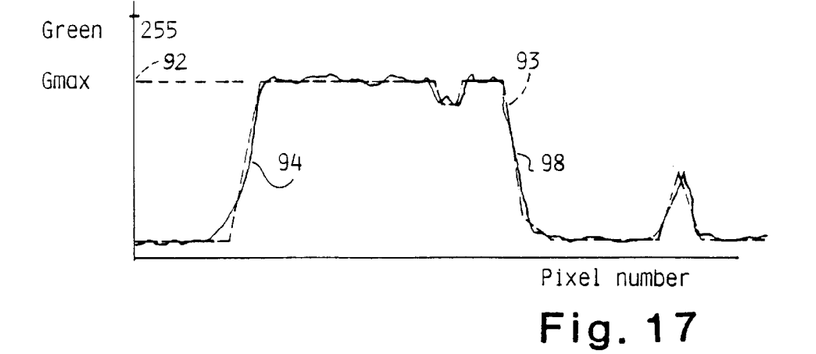

By repeating this process at each of the search lines 91, a sequence of points 95 on the subcutaneous fat 85 is derived, FIG. 16. A third order polynomial 96 is fitted to these points along with 47 (endx, endy) and 48 (bottomx, bottomy), and any points 95 significantly in error front the polynomial are discarded. The polynomial so defined is then used to define a further set of search lines 97 across the fat layer 85, similar to the above technique. These search lines 97 provide fat profiles which are analysed in a very similar manner to that described above to locate the start 94 of the fat layer. The profile is then further analysed to locate a corresponding, maximum negative slope which defines the end 95 of the fat layer in FIG. 17. Having calculated the x and y co-ordinates of the start 94 and end 98 of the fat layer 85 at this location, the fat layer thickness is calculated from: $d=\sqrt{((|x2-x1|*xscale)^2+(|y2-y1|*yscale)^2)}$ where xscale and yscale are the dimensions of each pixel in the x and y directions.

The fat layer thickness can be calculated by the above technique at any specified location on the subcutaneous fat boundary. Current techniques applied are to take several, equally spaced measurements. A further technique is as specified in the Ausmeat system, to locate the position on the subcutaneous fat boundary, ¾ of the length of the ribeye muscle away from the sawn chine and to measure fat depth perpendicular to the edge at this position.

Alternatively, an "average" fat depth may be determined by dividing a specified area of fat along the edge of the section, by a perimeter length volume.

SYSTEM CALIBRATION

Dimensional calibration is relatively straightforward in that an object of known size is viewed at the same position as occupied by the rib section and its x and y dimensions measured in terms of image pixels. This provides scale calibrations xscale and yscale in mm/pixel which remain fixed as long as the camera lens 23 and distance to the section 12 remain constant.

Of more critical importance is the 'colour' calibration of the system to ensure that any colour thresholds used, and also the absolute colour measurements can compensate for any changes in illumination intensity (eg lamp aging), camera electronic drift or image digitiser electronic drift. The calibration is also necessary to account for the small variations in illumination across the field of view, as the required resolution for meat and fat colour measurement is less than these variations.

A preferred calibration procedure may be as follows:

1. A lens cap is placed over the camera lens, thus stopping all light from entering the camera sensor. An offset adjustment is then iteratively made to the image digitiser electronics to ensure that this 'black' signal produces digitised values very close to zero in the RGB frame buffers.

2. A reference white board is placed in the camera frame in the same position as will be occupied by the rib sections to be assessed. A portion of the centre of this board is repeatedly digitised while recording the digitised RGB values and adjusting an electronic gain control on the image digitiser board. This is done until the maximum of the three RGB values is for example, 235±2.

Figure 18:
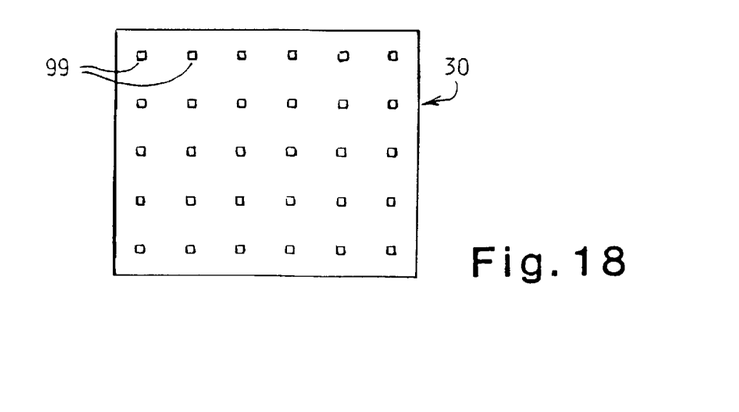
FIG. 18 shows a calibration board adapted to be used with the present invention.

3. An image 30 of the white board, under the final gain condition, is digitised and the RGB values from the image at a regular array of 'grid' positions 99 (see FIG. 18) are stored.

4. RGB values from images of reference gray and black boards are collected in the same manner as for the white board, thus producing a Red, Green and Blue value at each position 99 of the array from the white, gray and black boards. These values can be denoted, Rcalwij, Rcalgij, Rcalbij, Gcalwij etc.

5. Previous to the calibration, reference RGB values have been recorded from the three boards with the camera and frame grabber manually adjusted to provide correct colour measurement on a range of reference colour standards. These reference values are denoted Rrefw, Rrefg, Rrefb, Grefw etc in a similar fashion as for as the calibration values. Following a calibration as in 1–4 above, a quadratic equation is fitted to each set of Ref values (ie Red from white, gray, and black) with the reference values as the dependant variables and the three calibration values as the independent variables. In this way, the calibration values are 'corrected' back to the reference values. The same procedure is followed for the Green and Blue values at each site on the grid. In this way any subsequent colour measurement of RGB values at any position on the viewed area can be corrected back to the reference values using the derived quadratic equations. This method will account for any variability in camera sensitivity, gamma characteristics, lamp intensity or colour temperature variations etc. If the position of colour measurement is not exactly on the grid, then linear interpolation is used between the surrounding four points of the grid.

Also, if desired, a colour patch may be provided within the chiller assessment frame, to remain permanently within the field of view of the meat sample. By this means the software is able to make continuous corrections to the system calibration according to measurements made on the patch, and is also able to detect certain forms of system failure (eg loss of one of the colour signals). Additionally, the calibration methodology may provide for a master calibration reference, against which subsequent calibrations are compared. By this means a master calibration may be established by a suitable qualified technician and the system will check tolerance limits of all further calibrations against this to detect errors, correct operating procedures, etc. As day to day calibrations are undertaken by the ultimate user of the system the calibration data is stored to file, and by this means any drift in calibration of the unit may be tracked.

What is claimed is:

1. A process for identifying a target section within an image composed of an array of pixels, the process including storing color data for each pixel indicative of color information at the respective part of the image, the process comprising the steps of:

(A) discriminating from the color data the pixels having a predetermined color characteristic of the target section, and from these discriminated pixels, creating a refined data set of color data for selected pixels, the refined data set comprising data for only those selected pixels which are adjacent at least one other selected pixel and so that the refined data set encompasses a refined image section in the general target area of the image where the target section is expected to be located, (B) excising from the refined data set at least one data set for a cluster of pixels representing an external image section which is adjacent to and contacting the target section but which does not form part of the target section, the excising step including:

(i) analysing the shape of the refined image section represented by the refined data set to identify concavities in the boundary of the refined image section, forming lines along which the refined image section is to be separated into sub-sections, the lines extending from each of the said concavities in the boundary to other points either on the boundary or located internally of the boundary of the refined image section to thereby divide the refined image section into sub-sections, identifying valid lines demarcating the target section from adjacent touching external image sections by at least one of the steps of examining properties of the lines and examining properties of the sub-sections formed by the lines, and retaining in the refined data set only those data representing pixels to one side of the valid lines representing the target section, and (C) processing the refined data set after the excising step (B) has been carried out as the final data set representing the target section of the image.

2. A process as claimed in claim 1 wherein said other points to which the lines from each of said concavities in the boundary extend comprise points represented by pixels not having the predetermined color characteristic of the target section and being located either at the boundary of the refined image section or located internally of the boundary of the refined image section.

3. A process as claimed in claim 2 wherein the image comprises an image of a section of meat and the target section comprises a ribeye muscle located within the image of the section of meat, and wherein the predetermined color characteristic of the target section is a color characteristic of meat tissue, and wherein the refined data set of color data includes data for those pixels having the predetermined color characteristic of meat tissue and which are adjacent at least one other selected pixel so that the refined data set encompasses a refined image section where the ribeye muscle is located.

4. A process as claimed in claim 1 wherein the image comprises an image of a section of meat and the target section comprises a ribeye muscle located within the image of the section of meat, and wherein the predetermined color characteristic of the target section is a color characteristic of meat tissue, and wherein the refined data set of color data includes data for those pixels having the predetermined color characteristic of meat tissue and which are adjacent at least one other selected pixel so that the refined data set encompasses a refined image section where the ribeye muscle is located, and wherein said other points to which the lines from each of said concavities in the boundary extend comprise points represented by pixels having a predetermined color characteristic of fat tissue and being points where fat tissue appears at the boundary of the ribeye muscle or points where intramuscular fat tissue appears internally of the boundary of the ribeye muscle.

5. A process as claimed in claim 1 wherein the analysing step comprises quantifying parameters of the concavities and selecting by analysis of these quantified parameters the concavities most likely to indicate locations where external image sections contact and appear in the image to merge with and form part of the target section.

6. A process as claimed in claim 1 wherein the step of examining the properties of the lines comprises evaluating at least one of the following indications of likely validity of each line:

(a) the length of the line, (b) the area of at least one of the two sub-sections formed by the line, (c) the color parameters of the pixels along the length of the line, and (d) a mathematical function relating the length of the line and a measure related to the size of the smaller of the two sub-sections formed by the line.

7. A process as claimed in claim 1 wherein the step of examining the properties of the lines comprises evaluating for each line, as an indication of likely validity of that line, the length of the line.

8. A process as claimed in claim 1 wherein the step of examining the properties of the lines comprises evaluating for each line, as an indication of likely validity of that line, the area of at least one of the two sub-sections formed by the line.

9. A process as claimed in claim 1 wherein the step of examining the properties of the lines comprises evaluating for each line, as an indication of likely validity of that line, the color parameters of the pixels along the length of the line.

10. A process as claimed in claim 1 wherein the step of examining the properties of the lines comprises evaluating for each line, as an indication of likely validity of that line, a mathematical function relating the length of the line and a measure related to the size of the smaller of the two sub-sections formed by the line.

11. A process as claimed in claim 1 wherein the step of examining the properties of the lines comprises forming internal lines between the boundary of the refined image section and individual pixels or clusters of pixels having color characteristics not matching the predetermined color characteristic of the target section, the step of examining properties further comprising analyzing the internal lines to discard individual internal lines having low probability of being located at a boundary in the image between the target section and an external image section.

12. A process as claimed in claim 1 wherein the step of processing the final data set after the excising step has been carried out includes the step of discriminating from the final data set the pixels having predetermined spectral characteristics and deriving a measure of those pixels having the predetermined spectral characteristics in relation to those pixels not having the predetermined spectral characteristics.

13. A process as claimed in claim 12 wherein the image comprises an image of a section of meat and the target section comprises a ribeye muscle located within the image of the section of meat, and wherein the predetermined color characteristic of the target section is a color characteristic of meat tissue, and wherein the refined data set of color data includes data for those pixels having the predetermined color characteristic of meat tissue and which are adjacent at least one other selected pixel so that the refined data set encompasses a refined image section where the ribeye muscle is located, and wherein the step of discriminating from the final data set representing the ribeye muscle comprises discriminating the pixels having the spectral characteristics of meat tissue and deriving a measure of those pixels representing meat tissues in relation to those pixels representing other tissues including fat tissues whereby the derived measure is a measure of the marbling of the ribeye muscle.

14. A process for identifying the ribeye muscle in an image of a meat portion, the image being composed of an array of pixels comprising stored color data for each pixel, the process comprising the steps of:

(A) determining an array smaller than and located entirely within the array constituting the image of the meat portion, said smaller array enclosing within itself a connected body of pixels having a predetermined color characteristic of meat, said body of pixels being known with high probability to include at least some of the pixels representing meat of the ribeye muscle, (B) starting from within the smaller array and using the connected body of pixels having the predetermined color characteristic of meat, creating for further analysis a refined data set of pixel data for touching pixels having the predetermined color characteristic of meat, (C) excising from the refined data set at least one data set for a cluster of pixels representing an external image section which is adjacent to and contacting the ribeye muscle but which does not form part of the ribeye muscle, the excising step including the step of analysing the shape of the refined image section represented by the refined data set to identify concavities in the boundary of the refined image section and analysing each of said concavities in the boundary for its probability of indicating a point where the ribeye muscle is touched by a adjacent muscle not being part of the ribeye muscle.

15. A process as claimed in claim 14 wherein said smaller array comprises a rectangular ribeye box having straight sides located within the array constituting the image of the meat portion.

16. A process as claimed in claim 15 wherein the image of the meat portion comprises a rectangular array of pixels, and wherein the ribeye box is located entirely within the rectangular array constituting the image of the meat portion with all four sides of the ribeye box being spaced inwardly from the four sides of the rectangular array constituting the image of the meat portion.

17. A process as claimed in claim 16 wherein each of the sides of the ribeye box are parallel to respective corresponding sides of the rectangular array constituting the image of the meat portion.

18. A process as claimed in claim 16 wherein the step of determining the smaller array constituting the ribeye box comprises the steps of searching the image data for the image of the meat portion to identify the largest object in the image and storing the boundary edge coordinates of the largest object, searching the boundary edge coordinates for predetermined key points in the shape of the boundary edge, and calculating the boundaries of the ribeye box from the key points and from past analyses of locations of the ribeye muscles in similar images.

19. A process as claimed in claim 15 wherein the excising step includes analysing the shape of the refined image section represented by the refined data set to identify concavities in the boundary of the refined image section, forming lines along which the refined image section is to be separated into sub-sections, the lines extending from each of the said concavities in the boundary to other points either on the boundary or located internally of the boundary of the refined image section to thereby divide the refined image section into sub-sections, identifying valid lines demarcating the ribeye muscle from adjacent touching muscle by at least one of the steps of examining properties of the lines and examining properties of the sub-sections formed by the lines, and retaining in the refined data set only those data representing pixels to one side of the valid lines representing the ribeye muscle.

20. A process for determining grading parameters of a carcass, comprising the steps of:

(a) obtaining an image which includes the ribeye of the carcass, the image being composed of an array of pixels providing color data representative of color information at the corresponding part of the image;

(b) discriminating pixels representing muscle tissue from pixels representing fat tissue on the basis of a pixel color characteristic threshold;

(c) identifying a cluster of muscle tissue pixels within the image that represents the ribeye and tracing the outline of the ribeye muscle to exclude an external image section representing muscle tissue which abuts but is not part of the ribeye, the step of excluding an external image section representing muscle tissue which abuts but is not part of the ribeye including the steps of: identifying concavities in the ribeye boundary, and rejecting a concavity as a potential site to commence a cut to excise an external image section according to a quantifiable parameter of the concavity in relation to the body of the ribeye muscle;

(d) determining the proportion of pixels within the ribeye outline representing fat relative to the total number of pixels within the ribeye outline to obtain a value of the percentage of intramuscular fat in the ribeye;

(e) measuring the value of at least one standard grading criterion for the ribeye image, the standard grading criterion selected from the group consisting of the area of the ribeye, the percentage of intramuscular fat in the ribeye, and the thickness of a subcutaneous fat layer on the ribeye at a predetermined position;

(f) providing a grading parameter predictive equation wherein the grading parameter is included as a dependent variable, and at least one of the standard grading criteria for the ribeye is included as an independent variable; and (g) solving the grading parameter predictive equation to provide a value for the grading parameter of the carcass.

21. An apparatus for determining grading parameters of a carcass, comprising:

(a) image acquisition means for obtaining an image which includes the ribeye of the carcass; (b) computing and storage means for:

(i) storing the image as an array of pixels providing data representative of information at the corresponding part of the image;

(ii) discriminating pixels representing muscle tissue from pixels representing fat tissue on the basis of a pixel color characteristic threshold;

(iii) identifying a cluster of muscle tissue pixels within the image that represents the ribeye and tracing the outline of the ribeye muscle to exclude external image sections representing muscle tissue which abuts but is not part of the ribeye, the computing and storage means for tracing the outline of the ribeye muscle including means for identifying concavities in the ribeye outline and means for rejecting a concavity as a potential site to commence a cut to excise an external image section representing muscle tissue which abuts but is not part of the ribeye according to a quantifiable parameter of the concavity in relation to the body of the ribeye muscle;

(iv) determining the proportion of pixels within the ribeye outline representing fat relative to the total number of pixels within the ribeye outline to obtain a value of the percentage of intramuscular fat in the ribeye;

(v) measuring the value of at least one standard grading criterion for the ribeye image, the standard grading criterion selected from the group consisting of the area of the ribeye, the percentage of intramuscular fat in the ribeye, the thickness of a subcutaneous fat layer on the ribeye at a predetermined position;

(vi) providing a grading parameter predictive equation wherein the grading parameter is included as a dependent variable, and at least one of the standard grading criteria for the ribeye is included as an independent variable;

(vii) solving the grading parameter predictive equation to provide a value for the grading parameter of the carcass; and (c) means for providing an output of the grading parameter of the carcass.

* * * * *